(12) United States Patent
Saez (10) Patent No.: US 10,064,920 B2
(45) Date of Patent: *Sep. 4, 2018

(54) METHOD FOR CONTROLLED OVARIAN STIMULATION USING FSH AND HCG

(71) Applicant: Ferring B.V., Hoofddorp (DK)

(72) Inventor: Joan-Carles Arce Saez, Dragør (DK)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,419

(22) Filed: Apr. 4, 2016

(65) Prior Publication Data

US 2016/0213751 A1 Jul. 28, 2016

Related U.S. Application Data

(62) Division of application No. 13/823,732, filed as application No. PCT/IB2011/002541 on Sep. 28, 2011, now Pat. No. 9,320,778.

(30) Foreign Application Priority Data

Sep. 29, 2010 (EP) .................................. 10251681

(51) Int. Cl.
  *A61K 38/24* (2006.01)
  *A61K 45/06* (2006.01)
(52) U.S. Cl.
  CPC .............. *A61K 38/24* (2013.01); *A61K 45/06* (2013.01)
(58) Field of Classification Search
  None
  See application file for complete search history.

(56) References Cited

U.S. PATENT DOCUMENTS

| 7,695,721 B1 | 4/2010 | Franks et al. | |
| 2004/0248784 A1 | 12/2004 | Filicori | |
| 2008/0119394 A1* | 5/2008 | Filicori | A61K 38/24 514/9.9 |

FOREIGN PATENT DOCUMENTS

| EP | 788799 A3 | 10/1998 |
| WO | WO2000067778 A1 | 11/2000 |
| WO | WO2001000227 A1 | 1/2001 |
| WO | WO2004105788 A1 | 12/2004 |

OTHER PUBLICATIONS

Ashkenazi et al.; "The value of GnRH analogue therapy in IVF in women with unexplained infertility"; Human Reproduction; 1989, 4(6), 667-669.
Balasch et al., "Clinical Assisted Reproduction: The Effect of Exogenous Luteinizing Hormone (LH) on Oocyte Viability: Evidence from a Comparative Study Using Recombinant Human Follicle-Stimulating Hormone (FSH) Alone or in Combination with Recombinant LH for Ovarian Stimulation in Pituitary-Suppressed Women Undergoing Assisted Reproduction", Journal of Assisted Reproduction and Genetics, 2001, 18(5), 250-256.
Berkkanoglu et al., "Clinical effects of ovulation induction with recombinant follicle-stimulating hormone supplemented with recombinant luteinizing hormone or low-dose recombinant human chorionic gonadotropin in the midfollicular phase in microdose cycles in poor responders", Fertil. Steril., 2007, 88(3), 665-9.
Byrd, "Cryopreservation, thawing, and transfer of human embryos", Semin. Reprod. Med., 2002, 2(1): 37-43.
Drakakis et al., "Early hCG addition to rFSH for ovarian stimulation in IVF provides better results and the cDNA copies of the hCG receptor may be an indicator of successful stimulation", Reproductive Biology and Endocrinology 2009, 7, 110.
Fehring et al., "Variability in the Phases of the Menstrual Cycle", J. Obstet. Gynecol. Neonatal Nurs., 2006, 35(3), 376-84.
Filicori et al.; "Stimulation and Growth of Antral Ovarian Fillicles by Selective LH Activity Administration in Women"; Journal of Clinical Endocrinology and Metabolism; 2002, 87(3) 1156-1161.
Filicori et al., "Modulation of folliculogenesis and steroidogenesis in women by graded menotrophin administration", Human Reproduction, 2002; 17(8), 2009-2015.
Mannaerts, "A double-Blind, Randomized, Dose-Finding Study to Assess the Efficacy of the Gonadotrophin-releasing Hormone Antagonist Ganirelix (Org 37462) to Prevent Premature Luteinizing Hormone Surges in Women Undergoing Ovarian Stimulation with Recombinant Follicle Stimulating Hormone (Puregon). The Ganirelix"; Human Reproduction, 1998, 13(11), 3023-3031.
Paulson et al.; "Addition of a Gonadotropin Releasing Hormone (GNRH) Antagonist and Exogenous Gonadotropins to Unstimulated in Vitro Fertilization (IVF) Cycles: Physilogic Observations and Preliminary Experience"; Journal of Assisted Reproduction and Genetics; vol. 11; No. 4; pp. 28-32 (1994).
WIPO, International Search Report dated Jan. 20, 2012, which issued in corresponding International Application No. PCT/IB2011/002541, 4 pages.
Daftary and Patki, Reproductive Endocrinology and Infertility, 2009, p. 206.
Decision of the Opposition Division in European Patent No. 2621517 and Minutes of Oral Proceedings, dated Dec. 19, 2017, 35 pages.
Filicori et al., "Low-dose human chorionic gonadotropin therapy can improve sensitivity to exogenous follicle-stimulating hormone in patients with secondary amenorrhea," Fertil. Steril, 1999, 72: 1118-1120.
Filicori et al., "Luteinizing Hormone Activity Supplementation Enhances Follicle-Stimulating Hormone Efficacy and Improves Ovulation Induction Outcome," J. Clin. Endocrinol. Metab, 1999, 84:2659-2663.
Filicori et al., "The use of LH activity to drive folliculogenesis: exploring uncharted territories in ovulation induction," Human Reprod, 2002, 8:543-557.

(Continued)

*Primary Examiner* — Christina M Borgeest
(74) *Attorney, Agent, or Firm* — Fish & Richardson P.C.

(57) ABSTRACT

A product comprising follicle stimulating hormone (FSH) and human chorionic gonadotropin (hCG) for the treatment of infertility.

16 Claims, 1 Drawing Sheet

(56) References Cited

OTHER PUBLICATIONS

Gonal-f Summary of Product Characteristics, Jul. 2009, 207 pages.
Notice of Opposition to European Patent No. EP 2621517, dated Mar. 17, 2016, 19 pages.
Opponent's Submissions in European Application No. 11778689.7, dated Sep. 20, 2017, 6 pages.
Patentee's Response to the Communication of the Notice of Opposition, dated Nov. 1, 2016, 16 pages.
Patentee's Submissions in Response to the Opponent's Submissions of Sep. 20, 2017 in European Application No. 11778689.7, dated Oct. 31, 2017, 3 pages.
Propst et al., Low-dose human chorionic gonadotropin may improve in vitro fertilization cycle outcomes in patients with low luteinizing hormone levels after gonadotropin-releasing hormone antagonist administration, Fertil. Steril, 2011 96:898-904.
Reply to the Summons to Oral Proceedings in European Application No. 11778689.7, dated Sep. 20, 2017, 15 pages.
Stockman et al., "Human chorionic gonadotropin in commercial human menopausal gonadotropin preparations," Fertility & Sterility, Jul. 1993, 60: 176-178.
Summons to Attend Oral Proceeding in European Application No. 11778689.7 and Annex to the Communication, dated Dec. 4, 2017, 8 pages.
Thuesen et al., "A randomized controlled doseresponse pilot study of addition of hCG to recombinant FSH during controlled ovarian stimulation for in vitro fertilization," Human Reproduction, 2012, 27: 3074-3084.
Van Horne et al., "Recombinant follicle-stimulating hormone (rFSH) supplemented with low-dose human chorionic gonadotropin compared with rFSH alone for ovarian stimulation for in vitro fertilization," Fertility & Sterility, Oct. 2007, 88: 1010-1013.

* cited by examiner

METHOD FOR CONTROLLED OVARIAN STIMULATION USING FSH AND HCG

This application is a continuation of U.S. application Ser. No. 13/823,732, which entered the National Phase on Mar. 14, 2013 as the National Phase under 35 U.S.C. § 371 of PCT International Application No. PCT/IB2011/002541, filed internationally on Sep. 28, 2011, which claims the benefit of European Application No. 10251681.2, filed Sep. 29, 2010. Each of the aforementioned prior applications is incorporated herein by reference in its entirety.

FIELD

The present invention relates to compositions and pharmaceutical products for the treatment of infertility.

BACKGROUND

Assisted reproductive technology (ART) techniques such as in vitro fertilisation are well known. These ART techniques generally require a step of controlled ovarian stimulation (COS), in which a cohort of around 7 to 17 follicles is stimulated to full maturity. Standard COS regimens include administration of gonadotrophins, such as follicle stimulating hormone (FSH) alone or in combination with luteinising hormone (LH) activity to stimulate follicular development, normally with administration of a GnRH analogue prior to and/or during stimulation to prevent premature LH surge. The pharmaceutical compositions generally used for COS include recombinant follicle stimulating hormone (FSH), urinary derived FSH, recombinant FSH+LH preparations, and urinary derived menotrophin [human menopausal gonadotrophin (hMG)] and highly purified human menopausal gonadotrophin (HP-hMG).

Recombinant and urinary FSH preparations include only FSH. HMG and HP-hMG preparations contain FSH and luteinising hormone (LH) activity. The LH activity can originate from LH or human chorionic gonadotropin, hCG, depending on the specific hMG preparation. For example, 75 IU of the HP-hMG preparation MENOPUR® corresponds to approximately 10 IU hCG with respect to LH-activity.

DESCRIPTION

The present applicants have sought to provide an optimised composition which includes FSH (e.g. recombinant FSH), and additional LH activity, for use in controlled ovarian stimulation. The optimised compositions may provide a higher amount of LH activity (provided by hCG) than is present in the known urinary derived hMG/HP-hMG preparations or the known recombinant FSH+LH preparations.

Thus, according to the present invention, there is provided a product (e.g. a pharmaceutical product) comprising follicle stimulating hormone (FSH), for example recombinant FSH, and human chorionic gonadotropin (hCG) for (use in) the treatment of infertility (and/or for controlled ovarian stimulation) in a subject, wherein the FSH is for administration at a dose of, or equivalent to, 75 to 250 IU FSH per day (e.g. at a dose of, or equivalent to, 100 IU FSH, 150 IU FSH, 200 IU FSH, or 225 IU FSH per day) starting on day one of treatment and continuing for two to twenty days (for example continuing for seven to thirteen days, for example nine to thirteen days); and the hCG is for administration at a dose of, or equivalent to, 40 to 160 IU hCG per day (e.g. at a dose of, or equivalent to, 50 or 100 or 150 IU hCG per day) starting on day one of treatment and continuing for two to twenty days (for example continuing for seven to thirteen days, for example nine to thirteen days, for example 10 to 13 days, for example 10 to 11 days). The product may be for administration 12 to 16, e.g. 13 to 15, e.g. 14 days after administration of (e.g. after initiation of administration of, e.g. after initiation of daily administration of) a GnRH agonist (e.g. SYNAREL®, LUPRON®, DECAPEPTYL®). The product may be for administration with a GnRH agonist. The product may be for administration prior to administration of a GnRH antagonist (e.g. GANIRELIX®, CETRORELIX®), for example for administration five or six days prior to administration of a GnRH antagonist. The product may be for administration with a GnRH antagonist. The product may be for administration to the subject (or patient) after the subject has been (pre-)treated with a pharmaceutical composition which suppresses endogenous gonadotropin production (e.g. after the subject has been (pre-)treated with a steroid, a GnRH agonist, a GnRH antagonist etc.). Herein, the term "pre-treated" or "pre-treatment" refers to administration of the pharmaceutical composition which suppresses endogenous gonadotropin production prior to day one of the treatment with FSH and hCG.

The FSH may be for administration at a dose of, or equivalent to, 75 to 200 IU FSH per day (e.g. at a dose of, or equivalent to, 150 IU FSH per day) starting on day one of treatment and continuing for two to twenty days (for example continuing for seven to thirteen days, for example nine to thirteen days). Preferably, the FSH is for administration at a dose of, or equivalent to, 140 to 160 IU FSH per day (e.g. at a dose of, or equivalent to, 150 IU FSH per day) starting on day one of treatment and continuing for two to twenty days (for example continuing for seven to thirteen days, for example nine to thirteen days). The FSH may be for administration at a dose of, or equivalent to, 90 to 110 IU FSH per day (e.g. at a dose of, or equivalent to, 100 IU FSH per day) starting on day one of treatment and continuing for two to twenty days (for example continuing for seven to thirteen days, for example nine to thirteen days). The FSH may be for administration at a dose of, or equivalent to, 190 to 235 IU FSH per day (e.g. at a dose of, or equivalent to, 200 IU FSH per day, or at a dose of, or equivalent to, 225 IU FSH per day) starting on day one of treatment and continuing for two to twenty days (for example continuing for seven to thirteen days, for example nine to thirteen days).

The hCG may be for administration at a dose of, or equivalent to, 75 to 160 IU hCG per day [starting on day one of treatment and continuing for two to twenty days (for example continuing for seven to thirteen days, for example nine to thirteen days, for example 10 to 13 days, for example 10 to 11 days)]. The hCG may be for administration at a dose of, or equivalent to, 40 to 110 IU hCG per day, for example at a dose of, or equivalent to, 40 to 75 IU hCG per day. The hCG may be for administration at a dose of, or equivalent to, 55 to 125 IU hCG per day, for example at a dose of, or equivalent to, 75 to 125 IU hCG per day, for example at a dose of, or equivalent to, 90 to 110 IU hCG per day. The hCG may be for administration at a dose of, or equivalent to, 125 to 160 IU hCG per day, for example at a dose of, or equivalent to, 140 to 155 IU hCG per day. Preferably the FSH is recombinant FSH. The hCG may be recombinant hCG.

As indicated above, it is known that a daily dose of 75 IU of the HP-hMG preparation MENOPUR® corresponds to approximately 10 IU hCG with respect to LH-activity. It is known that a daily dose of 450 IU HP-hMG (in the case of MENOPUR® meaning 450 IU LH-activity equivalent to approximately 60 IU hCG) may be effectively and safely administered to subjects undergoing controlled ovarian stimulation. However, there has been concerns that high serum LH levels could perhaps adversely affect the treatment (e.g. by reduced pregnancy rates and increased miscarriage rates). The present applicants unexpectedly found that administration of 50, 100 or even 150 IU hCG as a daily dose, together with 150 IU FSH, may provide effective controlled ovarian stimulation (COS) with no indications of a detrimental impact on the efficacy. The present applicants also surprisingly found that administration of 100 or even 150 IU hCG as a daily dose, together with 150 IU FSH, may provide a marked increase in the number of top-quality embryos compared to the conventional treatment protocol (Table I, IV). Herein, a top-quality embryo is defined as four to five cells on day 2, seven or more cells on day 3, equally sized blastomeres and ≤20% fragmentation on day 3 and no multinucleation.

The dose of FSH and hCG may start on day one of treatment and continue for two to twenty days, for example continue for 2, 3, 4, 5, 6, 7, 8, 9, 10, 11, 12, 13, 14, 15, 16, 17, 18, 19, or 20 days. The doses of FSH and hCG may start on day one of treatment and continue for seven to thirteen days, for example nine to thirteen days, for example 10 to 13 days, for example 10 to 11 days. The dose of FSH and hCG may be administered at a dose equivalent to the daily doses mentioned above. For example the composition may be for administration at a dose of 450 IU FSH every three days (e.g. for administration on days 1, 4, 7 and so on) and a dose of 150 IU hCG (or 300 IU hCG or 450 IU hCG) every three days (e.g. for administration on days 1, 4, 7 and so on). In another example, the composition may be for administration at a dose of (or equivalent to) 1050 IU FSH every seven days (e.g. for administration on days 7, 14 and so on) and a dose of (or equivalent to) 350 IU hCG (or 700 IU hCG or 1050 IU hCG) every seven days (e.g. for administration on days 7, 14, and so on).

Herein, the term "product" or "pharmaceutical product" includes compositions or pharmaceutical compositions including both FSH and hCG for administration together—for example a vial including FSH and hCG, a single dose (e.g. injectable) formulation including specified amounts of FSH and hCG (e.g. 150 IU FSH and 100 IU hCG), or a multi dose (e.g. injectable) formulation including multiple (e.g. five) daily doses of specified amounts of FSH and hCG (e.g. 750 IU FSH and 500 IU hCG). The term "product" also includes separate compositions or pharmaceutical compositions each including either FSH or hCG which are for administration separately (e.g. as separate injections) at the defined daily doses, for example a kit comprising a container (e.g. a vial) including one or more daily doses of FSH and a separate container (e.g. a second vial) including one or more daily doses of hCG. If the product includes separate compositions, the daily dose of FSH is for administration before, after, or at the same time as the daily dose of hCG, preferably within 6 hours, preferably within 60 minutes, more preferably within 1 to 10 minutes of administration of the daily dose of hCG.

Thus, the product of the invention may include a first composition comprising FSH, preferably recombinant FSH, for administration at a dose of 75 to 250 IU FSH per day (e.g. 100 IU FSH, 150 IU FSH, 200 IU FSH, or 225 IU FSH per day or e.g. a dose of 75 to 200 IU FSH per day, e.g. 140 to 160 IU FSH per day) starting on day one of treatment and continuing for two to twenty days (for example continuing for seven to thirteen days, for example nine to thirteen days, for example 10 to 13 days, for example 10 to 11 days); and a second composition comprising hCG for administration at a dose of 40 to 160 IU hCG per day (e.g. 50 or 100 or 150 IU hCG per day or e.g. a dose of 75 to 160 IU hCG per day) starting on day one of treatment and continuing for two to twenty days (for example continuing for seven to thirteen days, for example nine to thirteen days, for example 10 to 13 days, for example 10 to 11 days). The first and second compositions may be for administration simultaneously or separately. If the compositions are for administration separately, the daily dose of FSH may be for administration before or after the daily dose of hCG, preferably within 6 hours, preferably within 60 minutes, more preferably within 1 to 10 minutes of administration of the daily dose of hCG.

In a further embodiment the product of the invention may include a composition comprising FSH, preferably recombinant FSH, and hCG, for administration at a dose of 75 to 250 IU FSH (e.g. 100 IU FSH, 150 IU FSH, 200 IU FSH, or 225 IU FSH; or a dose of 75 to 200 IU FSH per day, e.g. 140 to 160 IU FSH) and 40 to 160 IU hCG per day (e.g. 50 or 100 or 150 IU hCG or e.g. a dose of 75 to 160 IU hCG per day) per day starting on day one of treatment and continuing for two to twenty days (for example continuing for seven to thirteen days, for example nine to thirteen days, for example 10 to 13 days, for example 10 to 11 days).

Preferably the product is for administration prior to administration of a high (ovulatory) dose of hCG (4,000 to 11,000 IU hCG, e.g. 5,000 IU hCG, 10,000 IU hCG etc.; or 150 to 350 microgram recombinant hCG, for example 250 microgram recombinant hCG) to induce final follicular maturation.

In an aspect of the present invention there is provided a composition comprising human chorionic gonadotropin (hCG) for use in the treatment of infertility, wherein the hCG is for administration at a dose of, or a dose equivalent to, 90 to 110 IU hCG per day starting on day one of treatment and continuing for two to twenty days, together with (e.g. administration of a daily dose of) follicle stimulating hormone (FSH), The hCG may be for administration at a dose of, or a dose equivalent to, 95 to 105 IU hCG per day, more preferably at a dose of, or a dose equivalent to, 100 IU hCG per day. The FSH may be for administration at a dose of, or a dose equivalent to, 75 to 250 IU FSH per day, for example 100, 150, 200, 225 IU hCG per day.

The composition may be for (daily) administration of hCG together with (e.g. daily administration of) follicle stimulating hormone (FSH) starting on day one of treatment and continuing for seven to thirteen days, for example nine to thirteen days, for example 10 to 13 days, for example 10 to 11 days). The composition may be for administration 12 to 16, e.g. 13 to 15, e.g. 14 days after administration of (e.g. after initiation of administration of, e.g. after initiation of daily administration of) a GnRH agonist (e.g. Synarel, Lupron, Decapeptyl). The composition may be for administration with a GnRH agonist. The composition may be for administration prior to administration of a GnRH antagonist (e.g. ganirelix, cetrorelix), for example for administration five or six days prior to administration of a GnRH antagonist. The composition may be for administration with a GnRH antagonist.

Herein the term "treatment of infertility" includes treatment of infertility by controlled ovarian stimulation (COS) or methods which include a step or stage of controlled ovarian stimulation (COS), for example Intra Uterine Insemination (IUI), in vitro fertilisation (IVF), or intracytoplasmic sperm injection (ICSI). The term "treatment of infertility" includes treatment of infertility by ovulation induction (OI) or by methods which include a step or stage of ovulation induction (OD. The term "treatment of infertility" includes treatment of infertility in a subject having tubal or unexplained infertility, including treatment of infertility in a subject having endometriosis, for example stage I or stage II endometriosis, and/or in a subject having anovulatory infertility, for example WHO type II anovulatory infertility, and/or in a subject with a partner with male factor infertility.

The product (or composition) may be for (use in) the treatment of infertility (and/or for controlled ovarian stimulation) in a subject having endometriosis, for example in a subject having stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil. Steril. 1997; 67, 817-8211.].

The product (composition) may be for (use in) the treatment of infertility (and/or for controlled ovarian stimulation) in a subject having normal serum FSH level of 1 to 12 IU/L in the early follicular phase.

The product (composition) may be for (use in) the treatment of infertility (and/or for controlled ovarian stimulation) in a subject aged 18 to 42 years, for example 25 to 37 years. The product may be for (use in) the treatment of infertility (and/or for controlled ovarian stimulation) in a subject having BMI>18 and BMI<35 kg/m², for example a subject having BMI>20 and BMI<25 kg/m².

According to the present invention in a further aspect there is provided a method of treatment of infertility (e.g. a method of controlled ovarian stimulation) in a (e.g. human) subject comprising a step of administering to the subject a dose of, or equivalent to, 75 to 250 IU follicle stimulating hormone (FSH) per day (e.g. at a dose of, or equivalent to, 100 IU FSH, 150 IU FSH, 200 IU FSH, or 225 IU FSH per day) and a dose of, or equivalent to, 40 to 160 IU human chorionic gonadotropin (hCG) per day (e.g. at a dose of, or equivalent to, 50 or 100 or 150 IU hCG per day) starting on day one of treatment and continuing for two to twenty days (for example, continuing for seven to thirteen days, for example nine to thirteen days, for example 10 to 13 days, for example 10 to 11 days). The method may include a further step of administration of a GnRH agonist 12 to 16, e.g. 13 to 15, e.g. 14 days prior to day one of the FSH/hCG treatment. The product may be for administration with a GnRH agonist. The product may be for administration prior to administration of a GnRH antagonist (e.g. ganirelix, cetrorelix), for example for administration five or six days prior to administration of a GnRH antagonist. The product may be for administration with a GnRH antagonist. The method of treatment may comprise a step of pre-treatment (i.e. pre-treating the subject) with a pharmaceutical composition which suppresses endogenous gonadotropin production (e.g. a steroid, a GnRH agonist, a GnRH antagonist etc.).

Preferably the method of treatment of infertility includes a further step of administering a high (ovulatory) dose of hCG (4,000 to 11,000 IU hCG, e.g. 5,000 IU hCG, 10,000 IU hCG etc.; or 150 to 350 microgram recombinant hCG, for example 250 microgram recombinant hCG) to the subject to induce final follicular maturation.

The hCG may be for administration at a dose of, or equivalent to, 75 to 160 IU hCG per day [starting on day one of treatment and continuing for two to twenty days (for example continuing for seven to thirteen days, for example nine to thirteen days, for example 10 to 13 days, for example 10 to 11 days)]. The hCG may be administered at a dose of, or equivalent to, 40 to 110 IU hCG per day, for example at a dose of, or a dose equivalent to, 40 to 75 IU hCG per day. The hCG may be administered at a dose of, or a dose equivalent to, 55 to 125 IU hCG per day, for example at a dose of, or equivalent to, 75 to 125 IU hCG per day, for example at a dose of, or equivalent to, 90 to 110 IU hCG per day. The hCG may be administered at a dose of, or equivalent to, 125 to 160 IU hCG per day, for example at a dose of, or equivalent to, 140 to 155 IU hCG per day. The FSH and hCG may be administered separately or together. If the FSH and hCG are administered separately, the daily dose of FSH may be for administration before or after the daily dose of hCG, preferably within 6 hours, preferably within 60 minutes, more preferably within 1 to 10 minutes of administration of the daily dose of hCG.

The FSH may be for administration at a dose of, or equivalent to, 75 to 200 IU FSH per day (e.g. at a dose of, or equivalent to, 150 IU FSH per day) starting on day one of treatment and continuing for two to twenty days (for example continuing for seven to thirteen days, for example nine to thirteen days). Preferably, the FSH may be administered at a dose of, or equivalent to, 140 to 160 IU FSH per day (e.g. at a dose of, or equivalent to, 150 IU FSH per day). The FSH may be administered at a dose of, or equivalent to, 90 to 110 IU FSH per day (e.g. at a dose of, or equivalent to, 100 IU FSH per day). The FSH may be administered at a dose of, or equivalent to, 190 to 235 IU FSH per day (e.g. at a dose of, or equivalent to, 200 IU FSH per day, or at a dose of, or equivalent to, 225 IU FSH per day).

The present applicants have unexpectedly found that treatment with 50, 100 or even 150 IU hCG as a daily dose, together with e.g. 150 IU FSH, may provide effective controlled ovarian stimulation (COS) with no indications of a detrimental impact on the efficacy. The present applicants have surprisingly also found that administration of e.g. 100 or 150 IU hCG as a daily dose, together with 150 IU FSH, may provide a marked increase in the resulting number of top-quality embryos compared to the conventional treatment protocol (Table I, IV). The applicants found that administration of e.g. 100 or 150 IU hCG (together with FSH) increased the number of day 3 top-quality embryos, compared to the conventional (control) protocol, or the lower (e.g. 50 IU) dose hCG. The highest number of day 3 top-quality embryos was found in the group given 150 IU of hCG per day, although this group did not have the highest fertilisation rate. This means that treatment with around 150 IU hCG increases the chances of developing a top quantity embryo, although treatment with doses of around 100 IU hCG gives the best chance of achieving an ongoing pregnancy in the same (retrieval) cycle.

The method may be for treatment of infertility (and/or for controlled ovarian stimulation) in a subject having tubal or unexplained infertility, including a subject having endometriosis, for example stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil. Steril. 1997; 67, 817-821.].

The method may be for treatment of infertility (and/or for controlled ovarian stimulation) in a subject having (normal) serum FSH level of 1 to 12 IU/L in the early follicular phase.

The method may be for treatment of infertility (and/or for controlled ovarian stimulation) in a subject aged 18 to 42 years, for example 25 to 37 years. The method may be for treatment of infertility (and/or for controlled ovarian stimulation) in a subject having BMI>18 and BMI<35 kg/m$^2$, for example a subject having BMI>20 and BMI<25 kg/m$^2$.

The present invention also finds use in methods of treatment of infertility which include or may include a step of freezing the embryo for later use. Patients undergoing fertility treatment may wish to freeze viable embryos for later use (e.g. for lifestyle or health treasons, or to reduce costs associated with repeating treatments). Relatively recent developments in embryo-freezing technology mean that the rates of survival have improved markedly from around 50% to a current survival rate of 80-90%. Nevertheless, there remains a need for improved methods of providing top-quality embryos for freezing and subsequent use for treatment of infertility.

As discussed herein, the applicants found that administration of e.g. 100 or 150 IU hCG (together with FSH) increased the number of day 3 top-quality embryos, compared to the conventional (control) protocol, or the lower (e.g. 50 IU) dose hCG. The highest number of day 3 top-quality embryos was found in the group given 150 IU of hCG per day.

According to the present invention in a further aspect there is provided a product (e.g. a pharmaceutical product) comprising follicle stimulating hormone (FSH), for example recombinant FSH, and human chorionic gonadotropin (hCG) for (use in) the treatment of infertility in a (e.g. human) subject to develop one or more top quality embryos, wherein the FSH is for administration at a dose of, or equivalent to, 75 to 250 IU FSH per day (e.g. at a dose of, or equivalent to, 100 IU FSH, 150 IU FSH, 200 IU FSH, or 225 IU FSH per day, or at a dose of or equivalent to 75 to 200 IU FSH per day) starting on day one of treatment and continuing for two to twenty days (for example continuing for seven to thirteen days, for example nine to thirteen days); and the hCG is for administration at a dose of, or equivalent to, 140 to 190 IU hCG per day (e.g. at a dose of, or equivalent to, 140 to 160 IU hCG per day, e.g. at a dose of, or equivalent to, 150 IU hCG per day) starting on day one of treatment and continuing for two to twenty days (for example continuing for seven to thirteen days, for example nine to thirteen days, for example 10 to 13 days, for example 10 to 11 days). The product may be for use in the treatment of infertility to develop one or more top quality embryos, wherein the treatment includes a further step of freezing at least one resulting top quality embryo.

According to the present invention in a still further aspect there is provided a method of developing a top quality embryo in a subject (e.g. a human subject) comprising a step of administering to the subject a dose of, or equivalent to, 75 to 250 IU follicle stimulating hormone (FSH) per day (e.g. a dose of, or equivalent to, 100 IU FSH, 150 IU FSH, 200 IU FSH, or 225 IU FSH per day, or at a dose of or equivalent to 75 to 200 IU FSH per day) and a dose of, or equivalent to, 140 to 190 IU human chorionic gonadotropin (hCG) per day (e.g. at a dose of, or equivalent to, 140 to 160 IU hCG per day, e.g. at a dose of, or equivalent to, 150 IU hCG per day) starting on day one of treatment and continuing for two to twenty days (for example, continuing for seven to thirteen days, for example nine to thirteen days, for example 10 to 13 days, for example 10 to 11 days).

According to the present invention in a further aspect there is provided composition comprising human chorionic gonadotropin (hCG) for use in the treatment of infertility, wherein the hCG is for administration at a dose of, or a dose equivalent to, 140 to 190 IU hCG per day (e.g. a dose of, or a dose equivalent to, 140 to 160 IU hCG per day, e.g. a dose of, or a dose equivalent to, 150 IU hCG per day) starting on day one of treatment and continuing for two to twenty days, together with follicle stimulating hormone (FSH).

The applicants have found that supplementing FSH with e.g. 150 IU hCG may markedly improve the likelihood of developing of a top quality embryo.

The product (the doses of FSH/hCG) may be for administration to the subject after the subject has been pre-treated with a pharmaceutical composition which suppresses endogenous gonadotropin production (e.g. after the subject has been pre-treated with a steroid, a GnRH agonist, a GnRH antagonist etc.).

FSH can be obtained by any means known in the art, although recombinant FSH is preferred. Recombinant FSH products are known, for example PUREGON® (Organon), GONAL-F® or the human cell line derived FSH disclosed in WO2009/127826. FSH, as used herein, includes human-derived and recombinant FSH. Human-derived FSH can be purified from any appropriate source (e.g. urine) by any method known in the art. Methods of expressing and purifying recombinant FSH (e.g. from CHO or human cell lines) are known in the art. It will be appreciated that while recombinant FSH is preferred, the compositions of the invention may be provided using human derived FSH preparations such as hMG and HP-hMG. In this case some hCG activity may be provided by the human derived FSH; this may be supplemented to provide a composition of the invention by addition of hCG, as is readily understood by one skilled in the art.

hCG can be obtained by any means known in the art. hCG as used herein includes human-derived and recombinant hCG. Human-derived hCG can be purified from any appropriate source (e.g. urine, and placenta) by any method known in the art. Methods of expressing and purifying recombinant hCG are well known in the art.

The (pharmaceutical) product may be for the treatment of infertility, e.g. for use in assisted reproductive technologies (ART), ovulation induction or intrauterine insemination (IUI). The product may be used, for example, in medical indications where known FSH only preparations as well as preparations containing both FSH and LH activity such as urinary FSH, hMG and HP-hMG are used. The active ingredients of the products, doses and methods of the invention (i.e. FSH and hCG) can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non-toxic excipients, including salts, sugars, amino acids, surfactants, preservatives, stabilisers, isotonicity agents, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others. Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as castor oil), and injectable organic esters such as ethyl oleate. The products (and doses and compositions) of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of FSH and/or hCG from subcutaneous or intramuscular injection. This can be accomplished by the use of a liquid suspension of crystalline or amorphous material with poor water solubility. The rate of absorption of FSH and/or hCG then depends upon its rate of dissolution which, in turn, can depend upon crystal size and crystalline form. Alternatively, delayed absorption of a parenterally administered FSH and hCG combination form is accomplished by dissolving or suspending the FSH and hCG combination in an oil vehicle (such as castor oil). Injectable depot forms can be made by forming microencapsule matrices of the FSH and hCG (and other agents, if present) in biodegradable polymers such as polylactide-polyglycolide. Depending upon the ratio of FSH and hCG to polymer and the nature of the particular polymer employed, the rate of FSH and hCG release can be controlled. Examples of other biodegradable polymers include polyvinylpyrrolidone, poly (orthoesters), poly(anhydrides), hyaluronic acid etc. Depot injectable formulations are also prepared by entrapping the FSH and hCG in liposomes, microemulsions or nanosystems (like suspensions and emulsions) which are compatible with body tissues.

The products, compositions etc. of the invention may be formulated as semi solid films for example, for use as a transdermal patch.

A typical composition comprises a pharmaceutically acceptable carrier, such as aqueous solution, non-toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others. Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. The products (and doses and compositions) of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of FSH and/or hCG from subcutaneous or intramuscular injection. This can be accomplished by the use of a liquid suspension of crystalline or amorphous material with poor water solubility. The rate of absorption of FSH and/or hCG then depends upon its rate of dissolution which, in turn, can depend upon crystal size and crystalline form. Alternatively, delayed absorption of a parenterally administered FSH and hCG combination form is accomplished by dissolving or suspending the FSH and hCG combination in an oil vehicle. Injectable depot forms can be made by forming microencapsule matrices of the FSH and hCG (and other agents, if present) in biodegradable polymers such as polylactide-polyglycolide. Depending upon the ratio of FSH and hCG to polymer and the nature of the particular polymer employed, the rate of FSH and hCG release can be controlled. Examples of other biodegradable polymers include polyvinylpyrrolidone, poly(orthoesters), poly(anhydrides) etc. Depot injectable formulations are also prepared by entrapping the FSH and hCG in liposomes or microemulsions which are compatible with body tissues.

Injectable formulations and compositions can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like. Injectable formulations can be supplied as a product having pharmaceutical compositions including FSH and hCG, for administration separately or together. If administered separately, administration can be sequential. The product can be supplied in any appropriate package. For example, a product can contain a number of pre-filled syringes each including either FSH (a FSH composition), hCG (a hCG composition), or a combination of (a composition including) both FSH and hCG, e.g. the syringes packaged in a blister package or other means to maintain sterility. A product can optionally contain instructions for using the FSH and hCG formulations.

The pH and exact concentration of the various components of the product are adjusted in accordance with routine practice in this field. See GOODMAN and GILMAN's THE PHARMACOLOGICAL BASIS FOR THERAPEUTICES, $7^{th}$ ed. In a preferred embodiment, the products of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral products can be supplied in liquid formulation or as a solid which will be mixed with a sterile injectable medium just prior to administration. In an especially preferred embodiment, the parenteral products are supplied in unit dosage form for ease of administration and uniformity of dosage.

According to the present invention in a further aspect, there is provided a kit of parts for a product (e.g. a pharmaceutical product) for (use in) the treatment of infertility (and/or for controlled ovarian stimulation), the kit comprising at least one first container comprising one or more daily doses of follicle stimulating hormone (FSH), for example recombinant FSH, the or each daily dose comprising 75 IU to 250 IU FSH, (e.g. 100 IU FSH, 150 IU FSH, 200 IU FSH, or 225 IU FSH per day or e.g. a dose of, or equivalent to, 75 to 200 IU FSH per day, e.g. 140 to 160 IU FSH per day) for example 140 to 160 IU FSH (e.g. 150 IU FSH); and at least one second container comprising one or more daily doses of human chorionic gonadotropin (hCG), the or each daily dose of hCG comprising 40 to 160 IU hCG (e.g. 50 or 100 or 150 IU hCG or e.g. a dose of or equivalent to 75 to 160 IU hCG per day); wherein the daily doses of hCG and FSH are for administration starting on day one of treatment and continuing for two to twenty days (for example, continuing for seven to thirteen days, for example 10 to 13 days, for example 10 to 11 days). The kit may further comprise instructions (e.g. for administration). The kit may further comprise means for injection (e.g. syringe or syringes, needle or needles etc.).

The product may be for administration 12 to 16, e.g. 13 to 15, e.g. 14 days after administration of (e.g. after initiation of administration of, e.g. after initiation of daily administration of) a GnRH agonist (e.g. Synarel, Lupron, Decapeptyl). The product may be for administration with a GnRH agonist. The product may be for administration prior to administration of a GnRH antagonist (e.g. ganirelix, cetrorelix), for example for administration five or six days prior to administration of a GnRH antagonist. The product may be for administration with a GnRH antagonist. The (or each) daily dose of hCG may be, or be equivalent to, 75 to 160 IU hCG per day. The (or each) daily dose of hCG may be, or be equivalent to, 40 to 110 IU hCG per day, for example 40 to 75 IU hCG. The (or each) daily dose of hCG may be 55 to 125 IU hCG, for example 75 to 125 IU hCG, for example 90 to 110 IU hCG per day. The (or each) daily dose of hCG may be 125 to 160 IU hCG, for example 140 to 155 IU hCG. Preferably the FSH is recombinant FSH.

The present invention also provides the use of FSH, for example recombinant FSH, and hCG, in the manufacture of a medicament (e.g. a product) for the treatment of infertility (and/or for controlled ovarian stimulation), wherein the FSH is for administration at a dose of, or equivalent to, 75 IU to 250 IU FSH, (e.g. at a dose of, or equivalent to, 100 IU FSH, 150 IU FSH, 200 IU FSH, or 225 IU FSH or e.g. a dose of, or equivalent to, 75 to 200 IU FSH per day, e.g. 140 to 160 IU FSH per day) for example 140 to 160 IU FSH per day (e.g. at a dose of or equivalent to 150 IU FSH per day) starting on day one of treatment and continuing for two to twenty days (for example continuing for seven to thirteen days, e.g. nine to thirteen days, for example 10 to 13 days, for example 10 to 11 days); and the hCG is for administration at a dose of, or equivalent to, 40 to 160 IU hCG per day (e.g. at a dose of or equivalent to 50 or 100 or 150 IU hCG per day or e.g. a dose of or equivalent to 75 to 160 IU hCG per day) starting on day one of treatment and continuing for two to twenty days (for example continuing for seven to thirteen days, e.g. nine to thirteen days, for example 10 to 13 days, for example 10 to 11 days). The product may be administered 12 to 16, e.g. 13 to 15, e.g. 14 days after administration of (e.g. after initiation of administration of, e.g. after initiation of daily administration of) a GnRH agonist (e.g. Synarel, Lupron, Decapeptyl). The product may be for administration with a GnRH agonist. The product may be for administration prior to administration of a GnRH antagonist (e.g. ganirelix, cetrorelix), for example for administration five or six days prior to administration of a GnRH antagonist. The product may be for administration with a GnRH antagonist.

The products, compositions and methods of the invention mention specific doses of FSH and hCG, or doses equivalent to these. The doses are specified in terms of International Units of activity (IU), as is well known in the art. Herein the term "equivalent" means equal or substantially equal in terms of therapeutic activity. The skilled man readily understands how to calculate or determine the relevant dose or equivalent for any given FSH or hCG preparation.

DETAILED DESCRIPTION OF THE INVENTION

Figure 1:
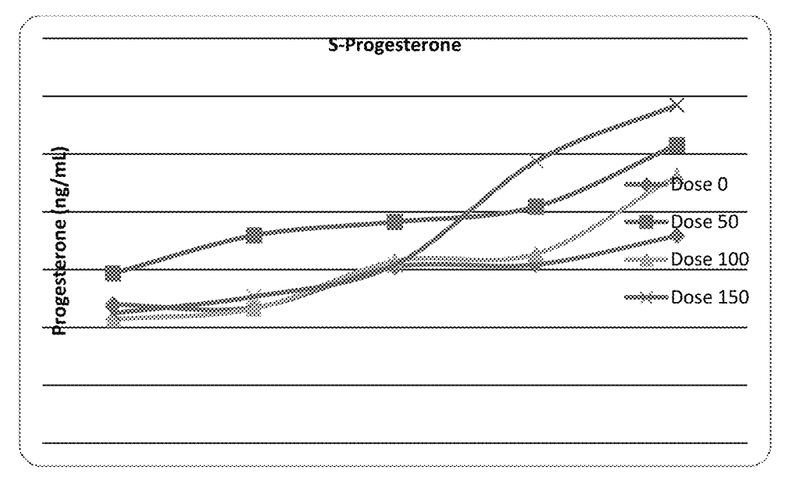
FIG. 1 is a plot showing the concentration (ng/mL) of progesterone in serum at stimulation days ("Stim") 1, 6, 10 and the day of induction of final follicular maturation administration with 10,000 IU Pregnyl (hCG), for the control and low, medium and high dose hCG arms in a human clinical trial.

The present invention will now be described in more detail with reference to FIG. 1 which shows the concentration (ng/mL) of progesterone in serum at stimulation days ("Stim") 1, 6, 10 and the day of induction of final follicular maturation administration with 10,000 IU Pregnyl (hCG), for the control and low, medium and high dose hCG arms.

The study was performed at the Fertility Clinic of the Copenhagen University Hospital in accordance with appropriate regulatory requirements as the ICH Harmonised Tripartite Guideline for GCP, existing Danish law and the ethical principles of the Declaration of Helsinki as adopted by the 18th World Medical Assembly in Helsinki, Finland, in 1964 and subsequent versions. This implies that the subjects were given both written and oral information and they had the opportunity to have an observer present at the information interview and they had time for reflection. Subjects could freely and at any time withdraw from the trial. The name and phone number of the investigator was given to the subject at the oral interview and in the written participant information. The information concerning the subjects are protected under Law regarding personal data and Health Act, Section 3 concerning patients' legal position.

The participating patients were women referred to the clinic to receive treatment for infertility. Those patients fulfilling the inclusion criteria were offered information about the trial.

The inclusion criteria for the study were as follows
1. Females with indication for COS and IVF;
2. Age between 25-37 years;
3. BMI>18 and <30 kg/m$^2$;
4. A regular menstrual cycle between 24 and 35 days and presumed to be ovulatory;
5. Two ovaries;
6. Tubal or unexplained infertility, including endometriosis stage I/II;
7. A uterus consistent with expected normal function (e.g. no clinically interfering uterine fibroids) documented by transvaginal ultrasound at the screening;
8. Male partner with sperm quality compatible with fertilization via IVF procedure or previous clinical pregnancy;
9. Early follicular phase serum FSH levels of 1-12 IU/l;
10. Early follicular phase total antral follicle (2-10 mm) count≥6;
11. Confirmation of down-regulation before randomisation by transvaginal ultrasound;
12. Willing and able to sign informed consent.

The exclusion criteria were as follows:
1. History of or current PCOS, endometriosis stage III/IV or severe male factor requiring ICSI;
2. History of severe ovarian hyperstimulation syndrome (OHSS);
3. Presence of unilateral or bilateral hydrosalpinx at ultrasound;
4. More than three previously COS cycles;
5. Previous poor response on an IVF-cycle, defined as >20 days of gonadotrophin stimulation, cancellation due to limited follicular response or less than four follicles of ≥15 mm diameter;
6. Previous IVF cycle with unsuccessful fertilization, defined as fertilisation of ≤20% of the retrieved oocytes;

7. History of recurrent miscarriage;
8. FSH>12 IU/L or LH>12 UI/L (early follicular phase);
9. Contraindications for the use of gonadotropins or GnRH analogues;
10. Recent history of current epilepsy, HIV infection, diabetes or cardiovascular gastrointestinal, hepatic, renal or pulmonary disease;
11. Pregnancy, lactation or contraindication to pregnancy;
12. Current past (last 12 months) abuse of alcohol or drugs;
13. History of chemotherapy (except for gestational conditions) of radiotherapy;
14. Undiagnosed vaginal bleeding;
15. Tumours of the ovary, breast, adrenal gland, pituitary or hypothalamus and malformation of sexual organs incompatible with pregnancy;
16. Abnormal karyotyping of the patient (if karyotyping is performed);
17. Hypersensitivity to any trial product.

The subjects underwent a screening process which included a full medical and gynaecological history (including infertility history); a transvaginal sonography with measurement of ovarian volume, number of antral follicles and thickness of endometrium, and confirmation of presence of both ovaries and exclusion of hydrosalpinx, endometriomas and ovarian abnormalities; full measurement of height, weight etc.; and blood sampling (FSH, LH and AMR).

For each subject, the GnRH agonist SYNARELA® (200 micrograms) was administered nasally at cycle day 21. Down-regulation was confirmed by transvaginal ultrasound at day 35 and defined as menstrual bleeding and the transvaginal ultrasound showing a shedded endometrium with a thickness of less than 5 mm and no ovarian cyst. Once down-regulation was confirmed each subject was randomized into one of four groups for the stimulation stage, as set out below (the groups are referred to as control arm, hCG low dose arm, hCG medium dose arm, or hCG high dose arm). The administration of GnRH antagonist was continued with the controlled ovarian stimulation below.

The controlled ovarian stimulation step commenced on cycle day 35 (herein "stimulation day 1", "treatment day 1" or "day 1 of treatment"). All subjects (n=62) were treated with recombinant FSH at 150 IU/day in the form of the commercially available preparation PUREGON® (N. V. Organon, Oss, The Netherlands) starting at day 1 of treatment (stimulation day 1). Subjects in the hCG low, medium and high dose arms were treated with the commercially available preparation hCG (PREDALON® Organon, Berlin, Germany) starting at day 1 of treatment (stimulation day 1), after the randomization.

The four study arms are:

| 1 | Control arm ("Dose 0" or "D0") | 150 IU/day of rFSH alone |
|---|---|---|
| 2 | hCG low dose ("Dose 50" or "D50") | 150 IU/day of rFSH and 50 IU/day of hCG from stimulation day 1/day 1 of treatment |
| 3 | hCG medium dose ("Dose 100" or "D100") | 150 IU/day of rFSH and 100 IU/day of hCG from stimulation day 1/day 1 of treatment |
| 4 | hCG high dose ("Dose 150" or "D150") | 150 IU/day of rFSH and 150 IU/day of hCG from stimulation day 1/day 1 of treatment |

On stimulation Day 1, the study nurse instructed the patient how to mix the medicine. The patient was instructed to open a new PREDALON® 500 IU ampoule every day, and dilute this as appropriate, prior to administration. In other words in this study the FSH and hCG where administered in the same injection. The dose of rFSH was kept constant, irrespective of response in all patients, except in cases (n=3) where there was an imminent risk of OHSS, where it was permissible to reduce the dose of rFSH, after day 5.

The target for ovarian stimulation was set to be 7-15 oocytes at retrieval and the maximum total duration of stimulation was 20 days. Preferably the length of stimulation [i.e. administration of FSH in all study arms, and hCG in study arms 2, 3 or 4] was from 9 to 13 days. Ultrasounds were performed at day 1, 6, 8 and 10 and the day of inducing final follicular maturation. Between day 10 and the day of inducing final follicular maturation with an ovulatory dose of hCG the patient was scanned every second or third day. The ultrasound was used to measure the number and size categories of each follicle during stimulation. The ultrasound was also used to measure the endometrial thickness, the triple-layer pattern, and echogenicity, on day 1, day 6 and the last stimulation day. When the ultrasound scan showed there were ≥3 follicles at ≥17-18 mm size a high dose of hCG (10,000 IU Pregnyl, N. V. Organon, Oss, The Netherlands) was administered that evening or one day after to induce final follicular maturation; this high dose is well known in the art.

Blood samples were collected at day 1, 3, 6, 8, 10 and the day of induction of final follicular maturation, as well as on the days where ultrasound scans were performed. The blood samples were used for assessment of hCG, FSH, LH, estradiol, progesterone, androstenedione, total testosterone, sex hormone-binding globulin (SHBG), inhibin B and anti-Mullerian Hormone (AMH). Blood samples were centrifuged 12 minutes at 3000×g and serum was stored individually at −18° C. and later analysed with all samples quantified in the same run. The analyses of hCG, androstenedione and progesterone were done at Laboratorium für Klinische Forschung (LKF; Raisdorf, Germany). Estradiol, FSH, LH and AMH were analysed at Department of Clinical Biochemistry, Rigshospitalet, Denmark.

For each patient, oocyte retrieval and embryo transfer were performed in the usual manner. Oocyte retrieval took place 36 h (±2 h) after induction of final follicular maturation with r-hCG administration. Follicular fluid from all follicles was collected and the volume assessed for each individual follicle. It was recorded whether an oocyte was obtained from the follicle or not. Assessment of cumulus mass appearance and collection of some (luteinized) granulosa and cumulus cells was performed at oocyte retrieval.

Insemination via regular IVF took place at 3 h (±2 h) after oocyte retrieval according to usual clinical procedure.

All oocytes were followed individually and quality assessed on the day of retrieval, and days 1, 2 and 3 after oocyte retrieval. Fertilization and embryo quality was assessed (using an inverted microscope) at 20 h (±2 h), 26 h (±2 h), 44 h (±2 h) and 68 h (±2 h) after oocyte retrieval. The embryo quality evaluation consisted of assessment of cell number and three parameters of embryo morphology: degree of fragmentation, blastomere uniformity and multinucleation. The number of top-quality embryos was assessed: a top-quality embryo being defined as four to five cells on day 2, seven or more cells on day 3, equally sized blastomeres and ≤20% fragmentation on day 3 and no multinucleation. The definition of a "top quality embryo" is well known in the art.

One or two of the best embryos were transferred to the patient on day 3 after oocyte retrieval (the others being cryopreserved for use in Frozen Embryo Replacement FER). Two weeks after embryo transfer a pregnancy test was performed to confirm pregnancy. If this test was positive a ultrasound was performed five to six weeks after embryo transfer. For the purpose of the study, a patient was considered completed in case of a negative s-hCG at day 13-15 after embryo transfer. In case of positive s-hCG the patient was scanned at clinical pregnancy (gestational week 7-8) and at ongoing pregnancy (gestational week 10-12). The clinical part of the study was formally closed at this time, but all pregnancies were (will be) followed until delivery. Additionally some patients who did achieve an ongoing pregnancy have cryopreserved unused embryos, and some patients who did not achieve an ongoing pregnancy still have unused cryopreserved embryos. All pregnancies were followed up to delivery. In addition, frozen embryos derived from the study were followed one year after study completion.

Vaginal progesterone was administrated as PROGESTAN® tablets 200 mg×3/day for luteal support from the day of embryo transfer until confirmation of pregnancy or negative serum βhCG test 13-15 days after embryo transfer. This is well known in the art.

Results

The results are shown in Tables I to VI. Table I includes data as of 10 Sep. 2010. Table II is similar to Table I updated to include data from the follow up one year after study completion, and is correct as of 17 Aug. 2011. The serum progesterone levels determined from the blood samples are shown in FIG. 1.

The study found that administration of 100 or even 150 IU hCG as a daily dose, together with 150 IU FSH, provides effective controlled ovarian stimulation (COS). The preliminary results of the study (Table 1) indicated that inclusion of hCG, in particular around 100 IU hCG to 150 IU hCG as a daily dose, together with e.g. 150 IU FSH may provide some optimisation compared to FSH alone. The study found no indications of a detrimental impact on ovarian response, embryo quality or pregnancy.

The clinical outcomes according to treatment groups are listed in Table I and II.

Oocyte retrieval was performed for all patients except from one patient in D100 because of no follicle development. Conversion to ICSI was done for one patient in D100 and one patient in D150. Transfer was not reached for seven patients due to no oocytes at retrieval, fertilisation failure and lack of transferable embryos. Blastocyst transfer on Day 5 was performed in two patients (D100, D150) because of abdominal pain and suspicion of infection on day 2 which delayed the transfer. Any infection was not confirmed.

The hCG medium dose group (D100) demonstrated the highest cumulated pregnancy rate per started fresh cycle (approx. 69%, Table 1).

The number of top-quality embryos per patient was analysed as a Poisson distributed count (Table IV). The mean number of top-quality embryos per patient was DO: 0.8±1.2, D50: 0.5±0.7, D100: 1.2±1.7 and D150: 1.5±1.7 (p=0.04). The mean values were compared for the four groups, and the D150 had a statistical significant higher mean count compared with D50 (Table IV). Thus, it was found that there was a significant influence of hCG on the number of day 3 top-quality embryos. The highest number was found in the group given 150 IU of hCG per day.

The hormone serum levels are presented in Table VI. Steady state level of s-hCG was reached on Day 6 of stimulation.

On the day of administering hCG to induce final follicular maturation ("Day of hCG", see Table VI), the serum hCG levels (IU/L) were DO: <0.1, D50: 3.1 (2.6-3.6), D100: 5.5 (4.1-7.4) and D150: 11.0 (8.9-13.6) (P<0.001). Thus, the serum level of hCG almost doubled when the hCG dose was increased by 50 IU. The levels of s-androstenedione increased significantly with higher doses of hCG. On the Day of hCG the two groups given the highest hCG doses had the highest s-estradiol levels (P=0.090). D150 had the highest s-progesterone and was significantly different from DO with the lowest value. The levels of FSH and LH did not vary between the groups.

The aim of the study was to find a dose of hCG that would reach the "ceiling level" above which some of the parameters measured would become less favourable to pregnancy. For progesterone, increasing the doses above 150 IU induced serum progesterone mean values reaching 1.2 ng/mL (see Table VI, FIG. 1). These approached the value of 1.5 µg/L which has been shown to decrease the frequency of ongoing pregnancy (Andersen, Devroey et al., 2006; Bosch, Labarta et al., 2010). It was also noted that the high dose hCG was associated with increased thickening of the endometrium, which is also perhaps associated with decreased frequency of ongoing pregnancy.

The results suggest that if the provision of a large number of top quality embryos is the main aim (e.g. to provide some embryos for subsequent freezing), then supplementation with e.g. 150 IU hCG (the higher dose) may be appropriate. However, if ongoing pregnancy in the retrieval cycle is also an aim, a dose of about 100 IU hCG may be more appropriate because this provides a combination of large number of top quality embryos, with the best chance of ongoing pregnancy.

Adverse Reactions/Events

Ovarian Hyperstimulation Syndrome (OHSS) was not seen in the two highest groups of hCG, suggesting further advantages of these doses; two patients one in each group DO and D50 respectively were diagnosed with OHSS. One patient in D50 had ovarian torsion. Blastocyst transfer on Day 5 was performed in two patients (D100, D150) because of abdominal pain and suspicion of infection on day 2 which delayed the transfer. Any infection was not confirmed. The total number of pregnancy losses was five due to ectopic pregnancy (2) and missed abortion (3).

TABLE I

IVF cycle outcome[1] in 60 per-protocol* FSH treated patients, according to hCG doses of 0, 50, 100 and 150 IU/day, administered as co-treatment from day 1 of stimulation.

|  | Dose 0 | Dose 50 | Dose 100 | Dose 150 |
| --- | --- | --- | --- | --- |
| Cycles | 16 | 15 | 16 | 13 |
| Aspirations | 16 | 15 | 15 | 13 |

TABLE I-continued

IVF cycle outcome[1] in 60 per-protocol* FSH treated patients, according to hCG doses of 0, 50, 100 and 150 IU/day, administered as co-treatment from day 1 of stimulation.

|  | Dose 0 | Dose 50 | Dose 100 | Dose 150 |
|---|---|---|---|---|
| Transfer | 14 | 14 | 15 | 10 |
| Treatment duration (days) | 10.25 | 9.33 | 9.88 | 10.80 |
| Total dose (IU) | 1538 | 1385 | 1475 | 1562 |
| Oocytes retrieved | 9.3 | 8.5 | 8.6 | 11.3 |
| Top-quality embryos per patient | 0.75 (12/16) | 0.47 (7/15) | 1.18 (19/16) | 1.50 (19/13) |
| Cryopreserved embryos (n) | 44 | 33 | 45 | 41 |
| Cryopreserved embryos per patient | 2.75 | 2.70 | 2.82 | 3.15 |
| Endometrial thickness (mm), day of hCG | 9.61 | 9.66 | 9.51 | 11.17 |
| Positive hCG/cycle started | 7/16 (43.8%) | 5/15 (33.3%) | 7/16 (43.8%) | 5/13 (38.5%) |
| Clinical pregnancy/cycle started | 4/16 (25.0%) | 4/15 (26.7%) | 6/16 (37.5%) | 5/13 (38.5%) |
| Ongoing pregnancy/cycle started | 4/16 (25.0%) | 4/15 (26.7%) | 4/16 (25.0%) | 4/13 (30.8%) |
| Multiple pregnancies after "fresh cycles" (n) | 0 | 0 | 0 | 0 |
| Number of FER[2] cycles per June 2010 | 6 | 7 | 8 | 2 |
| Positive hCG after FER/FER cycles | 1/6 (16.7%) | 2/7 (28.6%) | 4/8 (50%) | 1/2 (50%) |
| Ongoing pregnancy after FER (n) | 1 | 1 | 3 | 1 |
| Multiple pregnancies after FER (n) | 0 | 0 | 1 | 1 |
| Cumulated number positive hCG/started "fresh" cycle | 8/16 (50%) | 7/15 (46.7%) | 11/16 (68.8%) | 6/13 (46.2%) |
| Cumulated number ongoing pregnancy/started "fresh cycle" | 5/16 (31.3%) | 5/15 (33.3%) | 7/16 (43.8%) | 5/13 (38.5%) |
| Cumulated multiple pregnancies (n) | 0 | 0 | 1 | 1 |

*Two patients were withdrawn after randomization to 150 IU/day of hCG. They had their cycle cancelled respectively after 9 and 3 days of stimulation. This was due to major hCG dosing error. Instead of 150 IU/day, one patient injected 1500 IU daily during 3 days, the other patient injected 1500 IU at day 2 of stimulation.
[1]Data as of 1 Sep. 2010.
[2]FER means Frozen Embryo Replacement

TABLE II

Cycle outcome.

|  | Dose 0 (n = 16) | Dose 50 (n = 15) | Dose 100 (n = 16) | Dose 150 (n = 13) | P-value |
|---|---|---|---|---|---|
| Treatment duration (days) | 10.3 ± 1.4 | 9.3 ± 1.4 | 9.9 ± 1.3 | 10.4 ± 1.1 | 0.14 |
| Total dose of rFSH (IU) | 1538 ± 209 | 1385 ± 232 | 1475 ± 195 | 1562 ± 163 | 0.10 |
| Patients reaching oocyte retrieval [n (%)] | 16 (100) | 15 (100) | 15 (94) | 13 (100) | 0.42 |
| Oocytes retrieved/per retrieval | 9.3 ± 6.3 | 8.5 ± 4.4 | 9.2 ± 4.2 | 11.3 ± 5.7 | 0.53 |
| Fertilisation rate (%) [a] | 0.77 ± 0.27 | 0.72 ± 0.27 | 0.83 ± 0.23 | 0.67 ± 0.34 | 0.51 |
| Cleavage rate [b] | 0.72 ± 0.27 | 0.66 ± 0.27 | 0.77 ± 0.23 | 0.60 ± 0.34 | 0.41 |
| Patients with embryo transfer [n (%)] | 14 (88) | 14 (93) | 15 (94) | 10 (77) | 0.48 |
| Embryos transferred | 1.1 ± 0.27 | 1.1 ± 0.27 | 1.2 ± 0.41 | 1.0 ± 0.0 | 0.37* |
| SET [n (% per embryo transfer)] | 13 (93) | 13 (93) | 12 (80) | 10 (100) | 0.37 |
| Total implantation rate [c] (%) | 4/15 (27) | 4/15 (27) | 5/18 (28) | 4/10 (40) | 0.78 |
| Patients with embryos cryopreserved | 8 (50) | 8 (53) | 12 (75) | 8 (62) | 0.48 |
| Cryopreserved embryos per patient | 2.8 ± 3.7 | 2.2 ± 2.6 | 2.8 ± 2.4 | 3.2 ± 3.4 | 0.87 |
| Positive hCG/cycle started | 7 (44) | 5 (33) | 7 (44) | 5 (39) | 0.92 |
| Clinical pregnancy/cycle started | 4 (25) | 4 (27) | 6 (38) | 4 (31) | 0.87 |
| Live births [d]/cycle started | 4 (25) | 4 (27) | 4 (25) | 4 (31) | 0.98 |
| Number of FER cycles | 6 | 7 | 8 | 2 |  |
| Positive hCG after FER/FER cycles | 1 (17) | 2 (29) | 4 (50) | 1 (50) | 0.57 |
| Live births after FER (n) | 1 | 1 | 3 | 1 |  |
| Cumulated no. of live births [e]/started "fresh cycle" | 5 (31) | 5 (33) | 7 (44) | 5 (39) | 0.89 |

Values are mean ± SD or number (column percentage).

[a] Oocytes fertilized per intact oocyte retrieved.

[b] < cell day 2 per intact oocyte aspirated.

[c] Gestational sacs per embryos transferred.

[d] All fresh transfers were singletons.

[e] Two multiple pregnancies after FER.

*non parametric test

TABLE III

Stimulation characteristics.

|  | Dose 0 (n = 16) | Dose 50 (n = 15) | Dose 100 (n = 16) | Dose 150 (n = 13) | P-value |
|---|---|---|---|---|---|
| Day of hCG |  |  |  |  |  |
| Follicles ≤10 mm | 8.6 ± 4.8 | 7.7 ± 4.2 | 7.2 ± 4.2 | 7.9 ± 4.5 | 0.86 |
| Follicles 11-14 mm | 7.9 ± 5.8 | 6.7 ± 5.1 | 6.5 ± 4.0 | 5.3 ± 4.4 | 0.58 |
| Follicles ≥15 mm | 5.8 ± 2.0 | 6.4 ± 2.6 | 7.9 ± 3.6 | 7.5 ± 2.9 | 0.16 |
| Endometrium (mm) |  |  |  |  |  |
| Stimulation day | 13.0 ± 0.9 | 2.9 ± 1.0 | 2.6 ± 0.6 | 2.7 ± 0.8 | 0.48 |
| Stimulation day | 6.2 ± 1.7 | 6.8 ± 2.2 | 6.7 ± 1.6 | 6.8 ± 1.8 | 0.71 |
| Day of hCG | 9.6 ± 1.8 | 9.7 ± 2.3 | 10.1 ± 1.9 | 11.2 ± 2.5 | 0.20 |

Values are mean ± SD.

TABLE IV

Primary endpoint.

|  | Dose 0 (n = 16) | Dose 50 (n = 15) | Dose 100 (n = 16) | Dose 150 (n = 13) | P-value |
|---|---|---|---|---|---|
| Total no. of embryos (n) | 102 | 71 | 99 | 88 |  |
| Total no. of transferable embryos (n) | 49 | 35 | 58 | 47 |  |
| Total no. of top-quality embryos (n) | 12 | 7 | 19 | 19 |  |
| Embryos per patient[a] | 6.4 ± 4.7 | 4.7 ± 3.6 | 6.2 ± 4.3 | 6.8 ± 5.7 | 0.44 |
| Transferable embryos per patient[a] | 3.1 ± 3.9 | 2.3 ± 2.3 | 3.6 ± 2.6 | 3.6 ± 3.5 | 0.65 |
| Top-quality embryos per patient[a] | 0.8 ± 1.2 | 0.5 ± 0.7 | 1.2 ± 1.7 | 1.5 ± 1.7 | 0.23 |
| Top-quality embryos [b] | 0.8 ± 1.2 | 0.5 ± 0.7 | 1.2 ± 1.7 | 1.5 ± 1.7 | 0.04 |
| Patients with top-quality embryos [n (%)] | 6 (38) | 5 (33) | 8 (50) | 8 (62) | 0.43 |
| Top-quality embryos/oocytes retrieved (%) | 8.2 ± 13.2 | 6.1 ± 11.4 | 13.7 ± 16.8 | 12.3 ± 13.8 | 0.44 |

Values are mean ± SD or number (column percentage).
[a] ANOVA.
[b] Poisson distribution.

TABLE V

Primary endpoint. hCG levels on Day 6.

| hCG levels on stimulation Day 6 (IU/L) | 0.5-3.5 (n = 16) | 3.6-8.0 (n = 14) | 8.1-21.1 (n = 14) | P-value |
|---|---|---|---|---|
| Top-quality embryos per patient | 0.5 ± 0.9 | 1.1 ± 1.8 | 1.5 ± 1.5 | 0.03 [a] |

Values are mean ± SD.
[a] Poisson distribution

TABLE VI

Endocrine findings.

|  | Dose 0 (n = 16) | Dose 50 (n = 15) | Dose 100 (n = 16) | Dose 150 (n = 13) | P-value |
|---|---|---|---|---|---|
| hCG (UI/L) |  |  |  |  |  |
| Stimulation day 1 | <0.1 | <0.1 | <0.1 | <0.1 |  |
| Stimulation day 3 | <0.1 | 1.6 (1.2-2.1) | 3.1 (2.2-4.4) | 6.3 (5.2-7.7) | <0.01* |
| Stimulation day 6 | <0.1 | 2.2 (1.1-4.1) | 5.7 (4.4-7.5) | 10.5 (8.5-13.2) | <0.01* |
| Stimulation day 8 | <0.1 | 2.9 (2.3-3.6) | 5.8 (4.3-7.7) | 10.8 (8.5-13.8) | <0.01* |
| Stimulation day 10 | <0.1 | 2.8 (1.7-4.7) | 5.7 (3.9-8.3) | 11.2 (8.4-15.1) | <0.01* |
| Day of hCG | <0.1 | 3.1 (2.6-3.6) | 5.5 (4.1-7.4) | 11.0 (8.9-13.6) | <0.01 |
| Androstenedione (ng/mL) |  |  |  |  |  |
| Stimulation day 1 | 1.1 (0.9-1.2) | 1.3 (1.1-1.6) | 1.1 (0.9-1.4) | 1.1 (0.9-1.2) | 0.27 |
| Stimulation day 6 | 1.2 (1.0-1.4) | 1.8 (1.5-2.1) | 1.5 (1.3-1.9) | 1.5 (1.2-1.8) | 0.03 |
| Day of hCG | 2.1 (1.6-2.6) | 3.2 (2.3-4.5) | 4.0 (3.2-5.0) | 4.6 (3.5-6.1) | <0.01 |
| Progesterone (ng/mL) |  |  |  |  |  |
| Stimulation day 1 | 0.48 (0.38-0.59) | 0.59 (0.45-0.77) | 0.43 (0.34-0.55) | 0.45 (0.34-0.60) | 0.24 |
| Stimulation day 6 | 0.47 (0.39-0.57) | 0.72 (0.58-0.90) | 0.47 (0.36-0.60) | 0.51 (0.39-0.60) | 0.02 |
| Stimulation day 8 | 0.61 (0.49-0.76) | 0.77 (0.58-1.02) | 0.63 (0.51-0.78) | 0.62 (0.46-0.82) | 0.48 |

TABLE VI-continued

Endocrine findings.

|  | Dose 0 (n = 16) | Dose 50 (n = 15) | Dose 100 (n = 16) | Dose 150 (n = 13) | P-value |
|---|---|---|---|---|---|
| Stimulation day 1 | 0.62 (0.47-0.82) | 0.82 (0.53-1.26) | 0.66 (0.47-0.91) | 0.97 (0.72-1.31) | 0.09 |
| Day of hCG | 0.72 (0.58-0.89) | 1.03 (0.79-1.34) | 0.92 (0.79-1.08) | 1.17 (0.82-1.67) | 0.03 |
| Estradiol (nmol/L) | | | | | |
| Stimulation day 1 | <0.1 | <0.1 | <0.1 | <0.1 | |
| Stimulation day 3 | 0.2 (0.1-0.2) | 0.3 (0.1-0.4) | 0.2 (0.1-0.3) | 0.2 (0.1-0.2) | 0.31 |
| Stimulation day 6 | 0.8 (0.1-1.2) | 1.9 (1.2-3.0) | 1.3 (0.7-2.3) | 1.2 (0.7-2.0) | 0.09 |
| Stimulation day 8 | 1.7 (1.1-2.5) | 2.5 (1.1-5.5) | 3.4 (1.9-6.0) | 3.5 (2.4-5.2) | 0.19 |
| Stimulation day 10 | 4.1 (3.0-5.6) | 5.9 (3.5-9.8) | 4.6 (1.8-11.8) | 7.3 (4.1-13.1) | 0.41 |
| Day of hCG | 6.3 (3.7-10.8) | 10.0 (6.3-16.0) | 12.8 (9.5-17.2) | 12.0 (7.2-20.0) | 0.09 |
| FSH (UI/L) | | | | | |
| Stimulation day 1 | 3.0 (2.3-4.1) | 3.2 (2.5-4.1) | 3.1 (2.4-4.1) | 2.4 (1.7-3.2) | 0.43 |
| Stimulation day 3 | 8.9 (8.0-9.9) | 9.1 (8.3-9.9) | 8.8 (7.6-10.1) | 8.8 (7.8-9.9) | 0.97 |
| Stimulation day 6 | 11.6 (10.7-12.7) | 11.6 (10.5-12.9) | 11.7 (10.3-13.3) | 11.2 (10.1-12.4) | 0.93 |
| Stimulation day 8 | 11.7 (10.7-12.9) | 10.9 (8.7-13.6) | 11.9 (10.4-13.6) | 11.8 10.6-13.1) | 0.77 |
| Stimulation day 10 | 10.8 (9.8-12.1) | 12.5 (10.6-14.6) | 11.8 (9.7-14.2) | 12.5 (10.8-14.6) | 0.35 |
| Day of hCG | 11.2 (10.2-12.2) | 11.7 (10.4-13.2) | 10.9 (9.6-12.4) | 11.7 (10.4-13.1) | 0.73 |
| LH (UI/L) | | | | | |
| Stimulation day 1 | 3.0 (2.3-4.1) | 3.2 (2.5-4.1) | 3.1 (2.4-4.1) | 2.4 (1.7-3.2) | 0.43 |
| Stimulation day 3 | 2.1 (1.7-2.7) | 2.1 (1.6-2.8) | 2.1 (1.5-2.9) | 1.7 (1.3-2.2) | 0.48 |
| Stimulation day 6 | 1.9 (1.5-2.4) | 1.9 (1.4-2.8) | 1.7 (1.3-2.1) | 1.2 (0.8-1.9) | 0.15 |
| Stimulation day 8 | 1.7 (1.2-2.3) | 1.9 (1.2-3.0) | 2.2 (1.7-2.9) | 1.5 (1.0-2.1) | 0.35 |
| Stimulation day 10 | 1.9 (1.4-2.5) | 1.7 (0.9-3.4) | 2.3 (1.5-3.5) | 2.0 (1.2-3.4) | 0.72 |
| Day of hCG | 2.1 (1.5-2.9) | 1.9 (1.3-2.6) | 2.1 (1.6-2.8) | 1.5 (1.1-2.1) | 0.41 |

Values are mean and 95% CI. Absolute difference between the groups (%)
*Non parametric test Conclusion Supplementation with 100 or 150 IU hCG from the first day of stimulation may increase the pregnancy rate and/or the number of top-quality embryos.

The invention claimed is:

1. A method of developing a top quality embryo comprising a step of administering to a subject starting on day one and continuing for two to twenty days: a dose of, or equivalent to, 75 to 250 IU follicle stimulating hormone (FSH) per day; and a dose of, or equivalent to, 140 to 190 IU human chorionic gonadotropin (hCG) per day; and producing at least one top-quality embryo from and oocyte retrieved form the subject; wherein the at least one top quality embryo has four to five cells on day 2 after oocyte retrieval, seven or more cells on day 3 after oocyte retrieval, equally sized blastomeres and 20% fragmentation on day 3 after oocyte retrieval and no multinucleation.

2. A method according to claim 1, wherein the FSH is administered at a dose equivalent to, 100 and 200 IU FSH per day.

3. A method according to claim 2, wherein the hCG is administered at a dose equivalent to, 140 to 160 IU hCG per day.

4. A method according to claim 2, wherein the hCG is administered at a dose of, or a dose equivalent to, about 150 IU hCG per day.

5. A method according to claim 1, wherein the FSH is adiminstered at a dose equivalent to, about 150 IU FSH per day.

6. A method according to claim 5, wherein the hCG is administered at a dose of, or a dose equivalent to, about 150 IU hCG per day.

7. A method according to claim 1, wherein the hCG is administered at a dose equivalent to, 140 to 160 IU hCG per day.

8. A method according to claim 1, wherein the hCG is administered at a dose of, or a dose equivalent to, about 150 IU hCG per day.

9. A method according to claim 1, wherein the administering continues for seven to twenty days.

10. A method according to claim 1, wherein the administering continues for nine to thirteen days.

11. A method according to claim 1, wherein the administering continues for ten to eleven days.

12. A method according to claim 1, wherein the FSH is recombinant FSH.

13. A method according to claim 12, wherein the hCG is recombinant hCG.

14. A method according to claim 1, wherein the hCG is recombinant hCG.

15. A method according to claim 1, comprising a further step of administration of a gnRH agonist 12 to 16 days prior to day one of the FSH/hCG treatment.

16. A method according to claim 1, further comprising freezing at least one resulting top quality embryo.

* * * * *

UNITED STATES PATENT AND TRADEMARK OFFICE
CERTIFICATE OF CORRECTION

PATENT NO.        : 10,064,920 B2
APPLICATION NO.   : 15/090419
DATED             : September 4, 2018
INVENTOR(S)       : Joan-Carles Arce Saez It is certified that error appears in the above-identified patent and that said Letters Patent is hereby corrected as shown below:

In the Claims

In Claim 3 at Line 51, please delete: "A method according to claim 2,"
And insert: -- A method according to claim 1, --

In Claim 4, at Line 54, please delete: "A method according to claim 2,"
And insert: -- A method according to claim 1, --

In Claim 6, at Line 32, please delete: "A method according to claim 5,"
And insert: -- A method according to claim 2, --

In Claim 7, at Line 35, please delete: "A method according to claim 1,"
And insert: -- A method according to claim 2, --

In Claim 8, at Line 38, please delete: "A method according to claim 1,"
And insert: -- A method according to claim 3, --

In Claim 13, at Line 50, please delete: "A method according to claim 12,"
And insert: -- A method according to claim 1, --

In Claim 14, at Line 52, please delete: "A method according to claim 1,"
And insert: -- A method according to claim 12, --

Signed and Sealed this
Twenty-fourth Day of December, 2019

Andrei Iancu
*Director of the United States Patent and Trademark Office*